United States Patent
Chi et al.

(10) Patent No.: US 7,586,073 B2
(45) Date of Patent: Sep. 8, 2009

(54) IMAGING SYSTEM WITH HIGH-SPECTRUM RESOLUTION AND IMAGING METHOD FOR THE SAME

(75) Inventors: Chih-Wei Chi, Hsinchu (TW); Ding Kun Liu, Hsinchu (TW)

(73) Assignee: Industrial Technology Research Institute, Hsinchu County (TW)

( * ) Notice: Subject to any disclaimer, the term of this patent is extended or adjusted under 35 U.S.C. 154(b) by 0 days.

(21) Appl. No.: 11/757,281

(22) Filed: Jun. 1, 2007

(65) Prior Publication Data

US 2008/0225283 A1 Sep. 18, 2008

(30) Foreign Application Priority Data

Mar. 16, 2007 (TW) .............................. 96109046 A

(51) Int. Cl.
*G01J 1/32* (2006.01)
*H01L 31/14* (2006.01)
*F21V 9/00* (2006.01)

(52) U.S. Cl. ..................... 250/205; 250/553; 362/230

(58) Field of Classification Search .............. 250/208.1, 250/216, 221, 226, 214.1, 228, 552, 553, 250/205, 227.18; 356/604, 235, 236, 317, 356/341; 348/87, 181, 131–132; 362/89, 362/230–231, 237, 240, 245, 247, 234, 236, 362/543, 545; 382/141, 152, 162; 257/80, 257/82, 88, 89; 358/509–510, 520
See application file for complete search history.

(56) References Cited

U.S. PATENT DOCUMENTS

| 6,781,687 B2 | 8/2004 | Fisch et al. | |
|---|---|---|---|
| 6,857,762 B2 * | 2/2005 | Shimokawa et al. | 362/245 |
| 2002/0196338 A1 * | 12/2002 | Tham | 348/131 |
| 2004/0145753 A1 * | 7/2004 | Lim et al. | 356/602 |
| 2005/0088529 A1 * | 4/2005 | Geng | 348/207.99 |
| 2005/0237537 A1 * | 10/2005 | Leizerson et al. | 356/504 |
| 2005/0254066 A1 * | 11/2005 | Mamiya et al. | 356/604 |
| 2005/0254704 A1 * | 11/2005 | Komiya et al. | 382/162 |
| 2006/0072319 A1 * | 4/2006 | Dziekan et al. | 362/249 |

* cited by examiner

*Primary Examiner*—Georgia Y Epps
*Assistant Examiner*—Don Williams
(74) *Attorney, Agent, or Firm*—WPAT, P.C.; Anthony King

(57) ABSTRACT

An imaging system comprises a light source module configured to generate a combination beam, a controller configured to control the light source module, an image-capturing module configured to capture the reflected beam by a sample. The light source module comprises a plurality of light-emitting devices configured to emit lights of different wavelengths, and the controller is configured to drive the light-emitting devices to emit the lights to form the combination beam consisting of at least two lights of different wavelengths. An imaging method comprises the steps of forming a first combination beam consisting essentially of at least two lights of different wavelengths, capturing the reflected first combination beam by a sample to have a first image, forming a second combination beam consisting of at least two lights of different wavelengths and capturing the reflected second combination beam by the sample to have a second image.

14 Claims, 7 Drawing Sheets

IMAGING SYSTEM WITH HIGH-SPECTRUM RESOLUTION AND IMAGING METHOD FOR THE SAME

BACKGROUND OF THE INVENTION (A) Field of the Invention

The present invention relates to an imaging system and an imaging method for the same, and more particularly, to an imaging system with high-spectrum resolution and an imaging method for the same.

(B) Description of the Related Art

There is a certain technical bottleneck in the automatic optical inspection apparatus on differentiating objects with similar colors. For example, gold and copper in the printed circuit board have similar colors such that the automatic optical inspection apparatus cannot effectively inspect the defect such as poor plating gold or oxidized copper since one cannot clearly be differentiated from another. In particular, the uses of the broadband white light source of the automatic optical inspection apparatus prevent it from effectively differentiating objects with similar colors such as low-grade gold plating and oxidized copper.

U.S. Pat. No. 6,781,687 discloses an improved color image capturing system, which uses a black-and-white camera with twinkling triple-color light source to capture red-light image, green-light image and blue-light image, and a subsequent image-processing is performed to incorporate the red-light image, green-light image and blue-light image to form a clear color image for further recognition and analysis.

SUMMARY OF THE INVENTION

The present invention provides an imaging system with high-spectrum resolution and an imaging method for the same.

An imaging system with high-spectrum resolution according to one example of the present invention may comprise a light source module including a plurality of light-emitting devices configured to emit lights of different wavelengths, a controller configured to control the light source module to generate a combination beam and an image-capturing module configured to capture a reflected beam by a sample.

The present invention provides an imaging method with high-spectrum resolution comprising the steps of forming a first combination beam including at least two lights of different wavelengths, capturing a first reflected beam of the first combination beam by a sample to have a first image, forming a second combination beam including at least two lights of different wavelengths and capturing a second reflected beam of the second combination beam by the sample to have a second image.

The present invention uses the controller to drive the plurality of light-emitting devices to generate the combination beams that alternately irradiate on the sample, and uses the image-capturing module to capture the reflected beams from the sample under the irradiation of the combination beams. Consequently, the present invention can capture colorful images at high speed, and the colorful images can be applied to the automatic recognition system such as the inspection of the printed circuit board, flat display and the integrated circuit package.

BRIEF DESCRIPTION OF THE DRAWINGS

The objectives and advantages of the present invention will become apparent upon reading the following description and upon reference to the accompanying drawings in which.

DETAILED DESCRIPTION OF THE INVENTION

Figure 1:
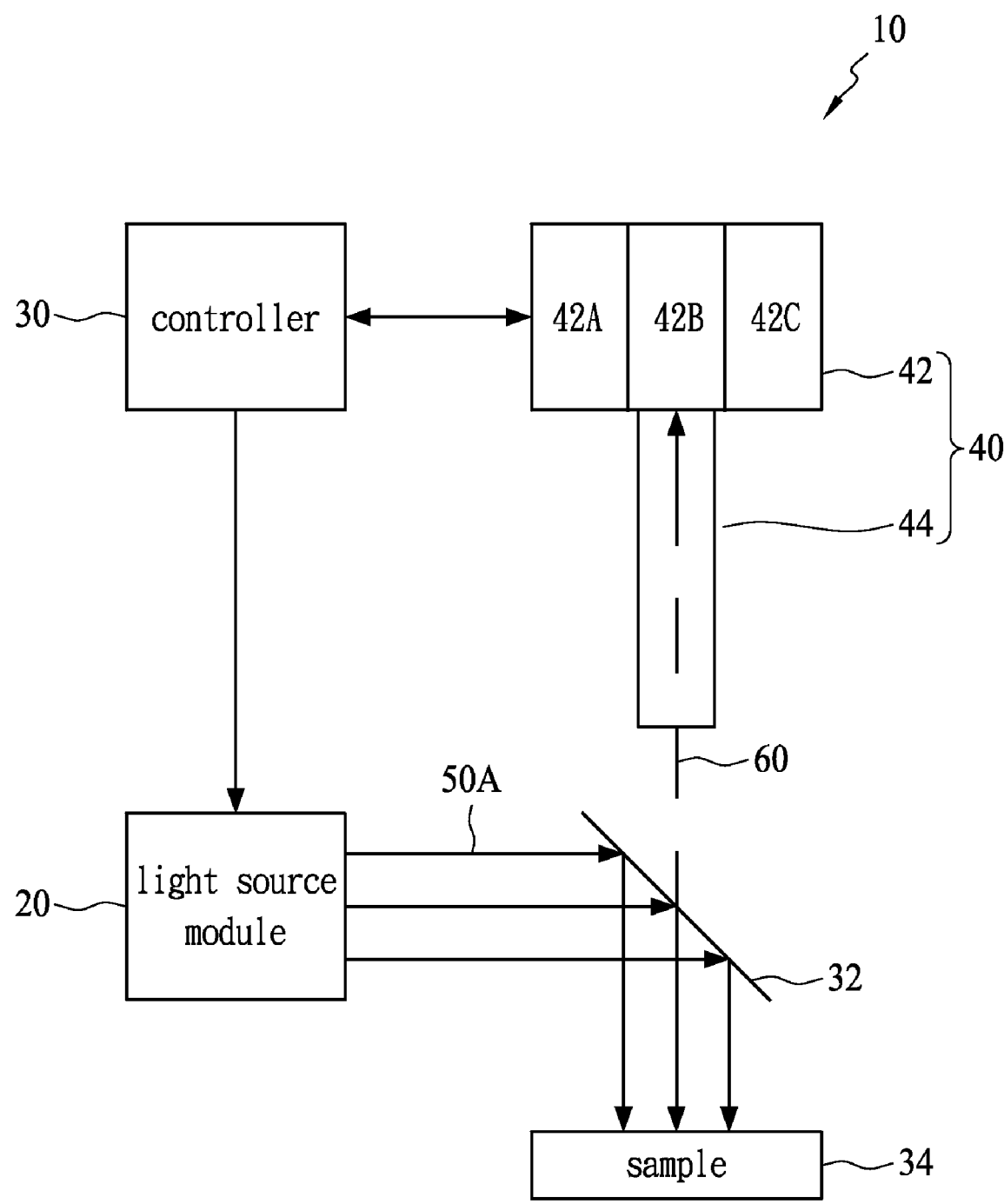
FIG. 1 to FIG. 5 illustrate an imaging system with high-spectrum resolution according to one embodiment of the present invention.

FIG. 1 to FIG. 5 illustrate an imaging system 10 with high-spectrum resolution according to one embodiment of the present invention. The imaging system 10 comprises a light source module 20, a controller 30 configured to control the light source module 20 to generate a combination beam 50A, a beam-splitting device 32 configured to direct the combination beam 50A to a sample 34 and allow a reflected beam 60 from the sample 60 to penetrate through, and an image-capturing module 40 configured to capture the reflected beam 60. The image-capturing module 40 includes an image sensor 42 and a lens 44, and the image sensor 42 includes a red-light charge coupled device 42A, a green-light charge coupled device 42B and a blue-light charge coupled device 42C.

Figure 2:
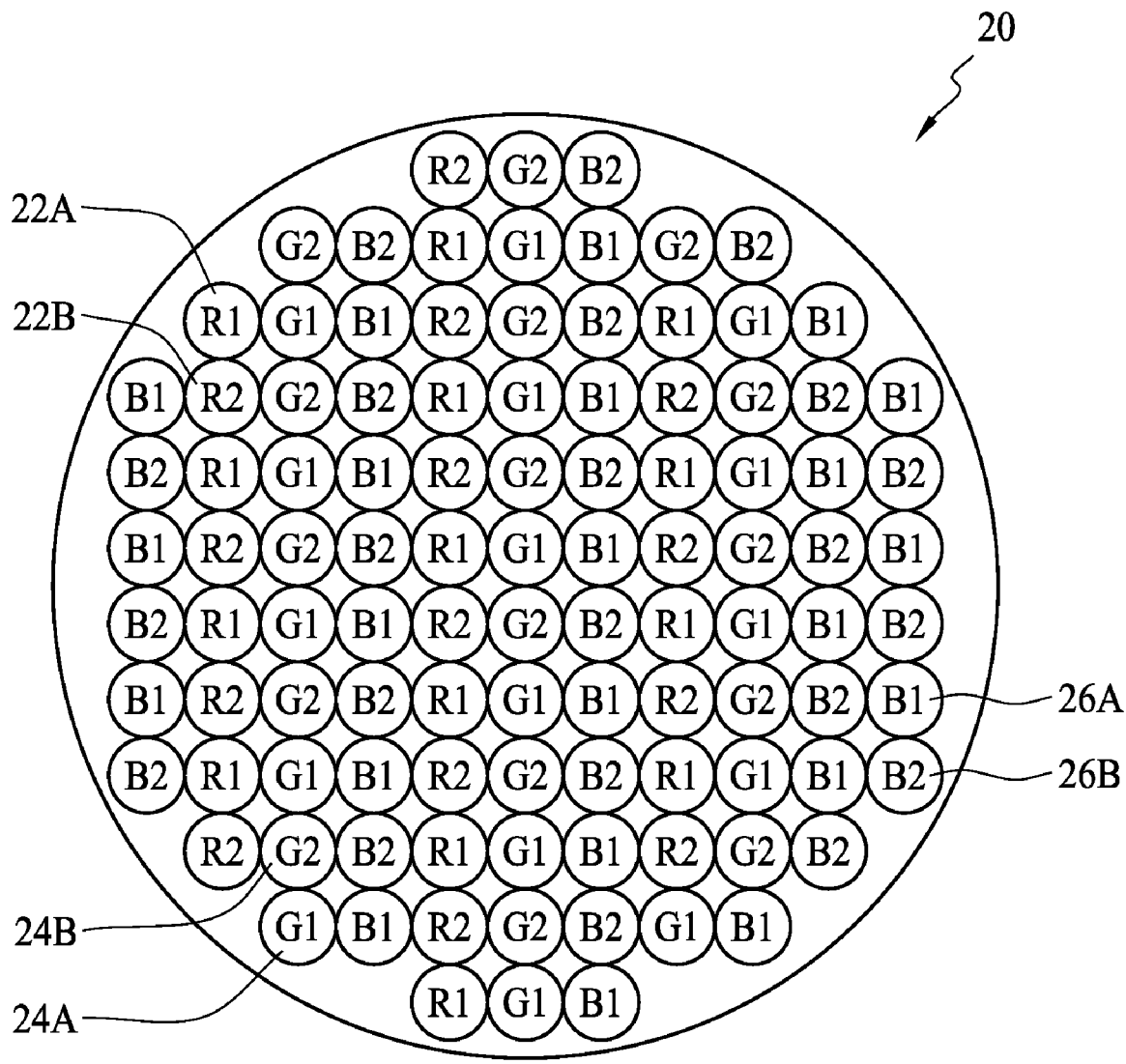
Figure 3:
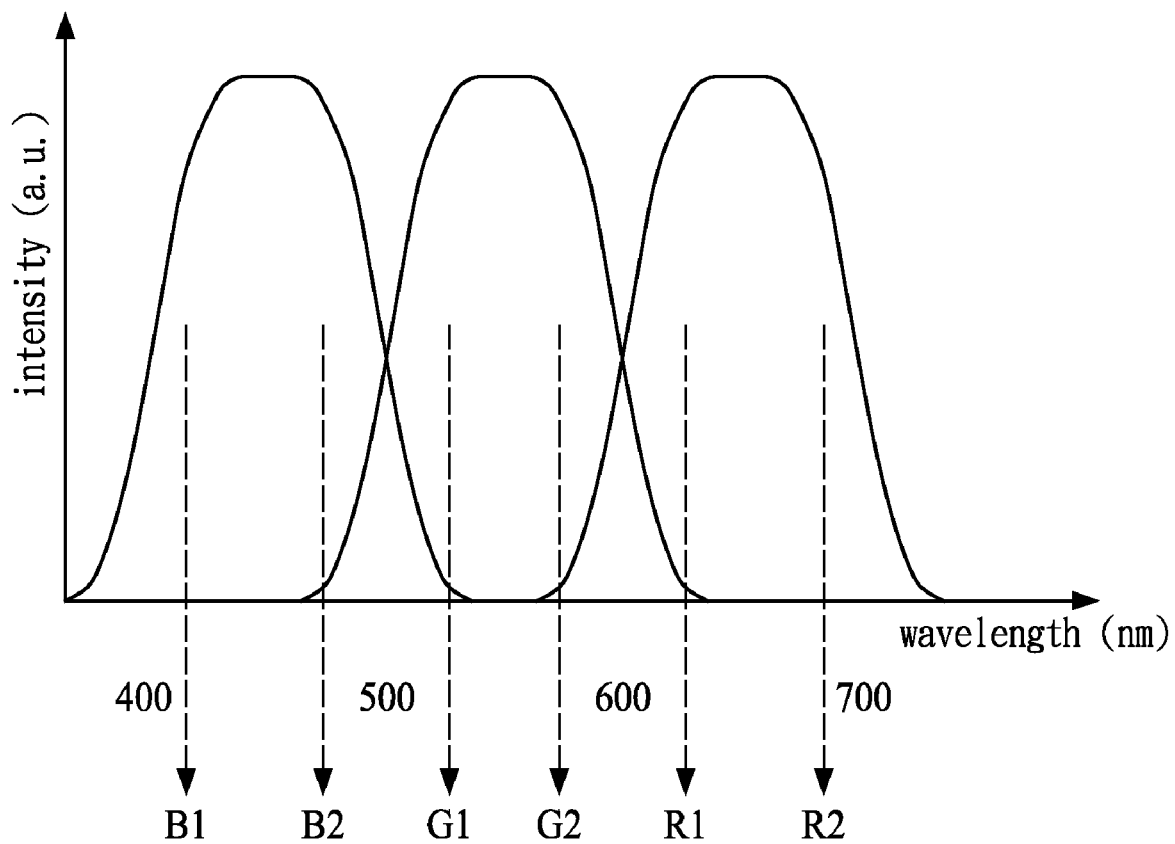

Referring to FIG. 2, the light source module 20 includes a plurality of light-emitting devices configured to emit lights of different wavelengths. For example, the light-emitting devices can be red light-emitting diodes 22A, 22B (R1, R2), green light-emitting diodes 24A, 24B (G1, G2) and blue light-emitting diodes 26A, 26B (B1, B2). The spectrums of the red light-emitting diodes 22A, 22B (R1, R2), the green light-emitting diodes 24A, 24B (G1, G2) and the blue light-emitting diodes 26A, 26B (B1, B2) are shown in FIG. 3. In particular, the red light-emitting diodes 22A, 22B (R1, R2), the green light-emitting diodes 24A, 24B (G1, G2) and the blue light-emitting diodes 26A, 26B (B1, B2) are arranged uniformly to generate the combination beam uniformly. Furthermore, the light-emitting devices can be laser or metal lamp.

Figure 4:
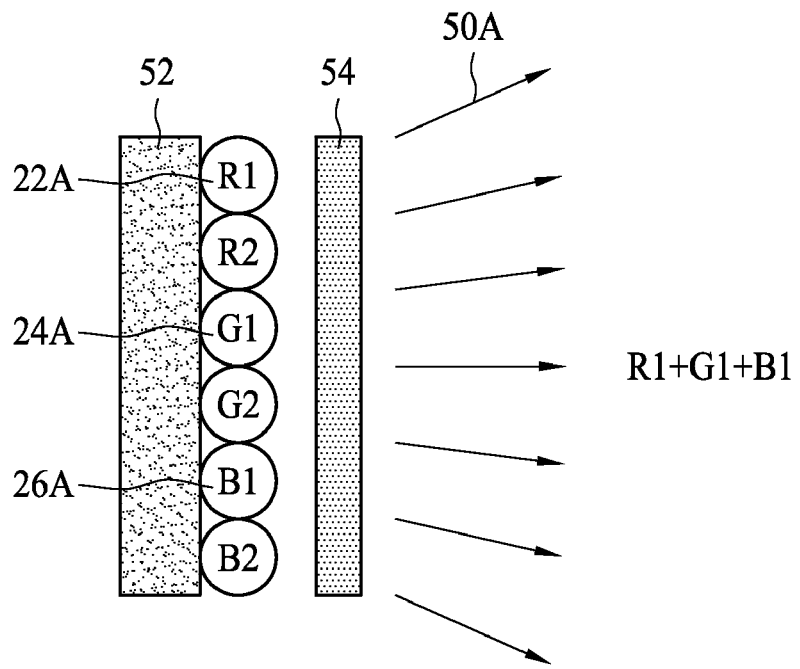
Figure 5:
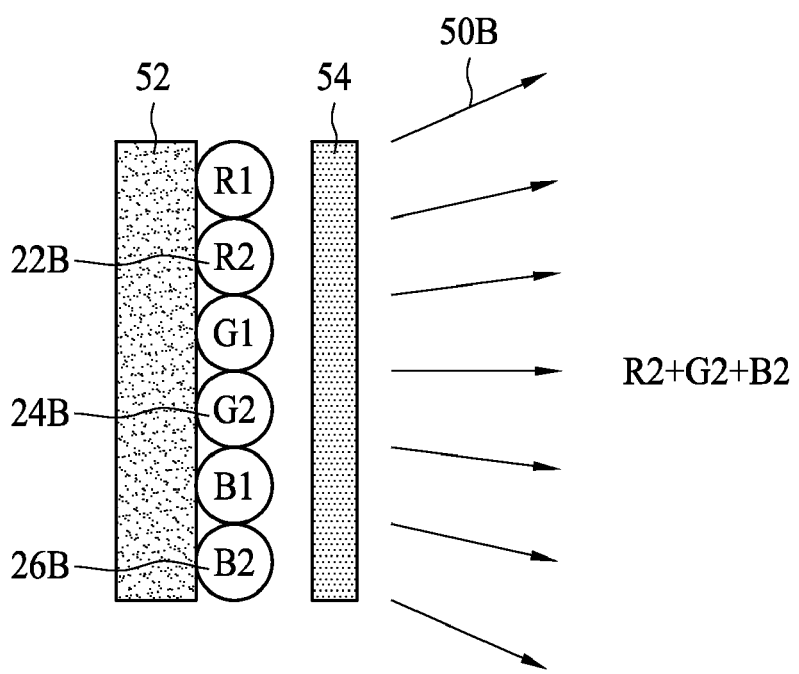

Referring to FIG. 4, the red light-emitting diodes 22A, 22B (R1, R2), the green light-emitting diodes 24A, 24B (G1, G2) and the blue light-emitting diodes 26A, 26B (B1, B2) are positioned in a plate 52. According to a predetermined program, the controller 30 can drive the red light-emitting diode 22A, the green light-emitting diode 24A, and the blue light-emitting diode 26A to emit lights simultaneously, and the lights are mixed by a mixing plate 54 to form the combination beam 50A including at least three lights (R1, G1, B1) of different wavelengths. The sample 34 reflects the combination beam 50A to form the reflected beam 60, and the image-capturing module 40 uses the red-light charge coupled device 42A, the green-light charge coupled device 42B and the blue-light charge coupled device 42C to detect the reflected beam 60 penetrating through the beam-splitting device 32 to form a first image (a first reflection spectrum). Referring to FIG. 5, after turning off the red light-emitting diode 22A, the green light-emitting diode 24A and the blue light-emitting diode 26A, the controller 30 then drives the red light-emitting diode 22B, the green light-emitting diode 24B and the blue light-emitting diode 26B to emit lights simultaneously, and the lights are mixed by the mixing plate 54 to form a combination beam 50B including at least three lights (R2, G2, B2) of different wavelengths. In particular, the combination beam 50A and the combination beam 50B have different spectrums. The sample 34 reflects the combination beam 50B to form the reflected beam 60, and the image-capturing module 40 uses the red-light charge coupled device 42A, the green-light charge coupled device 42B and the blue-light charge coupled device 42C to detect the reflected beam 60 penetrating through the beam-splitting device 32 to form a second image (a second reflection spectrum). The above-mentioned light-emitting method is one embodiment of the present invention only, the present invention can be implemented by using other combination of light-emitting devices, for example, by using two narrowband light-emitting devices for generating lights of different wavelength to form the combination beam.

Figure 6:
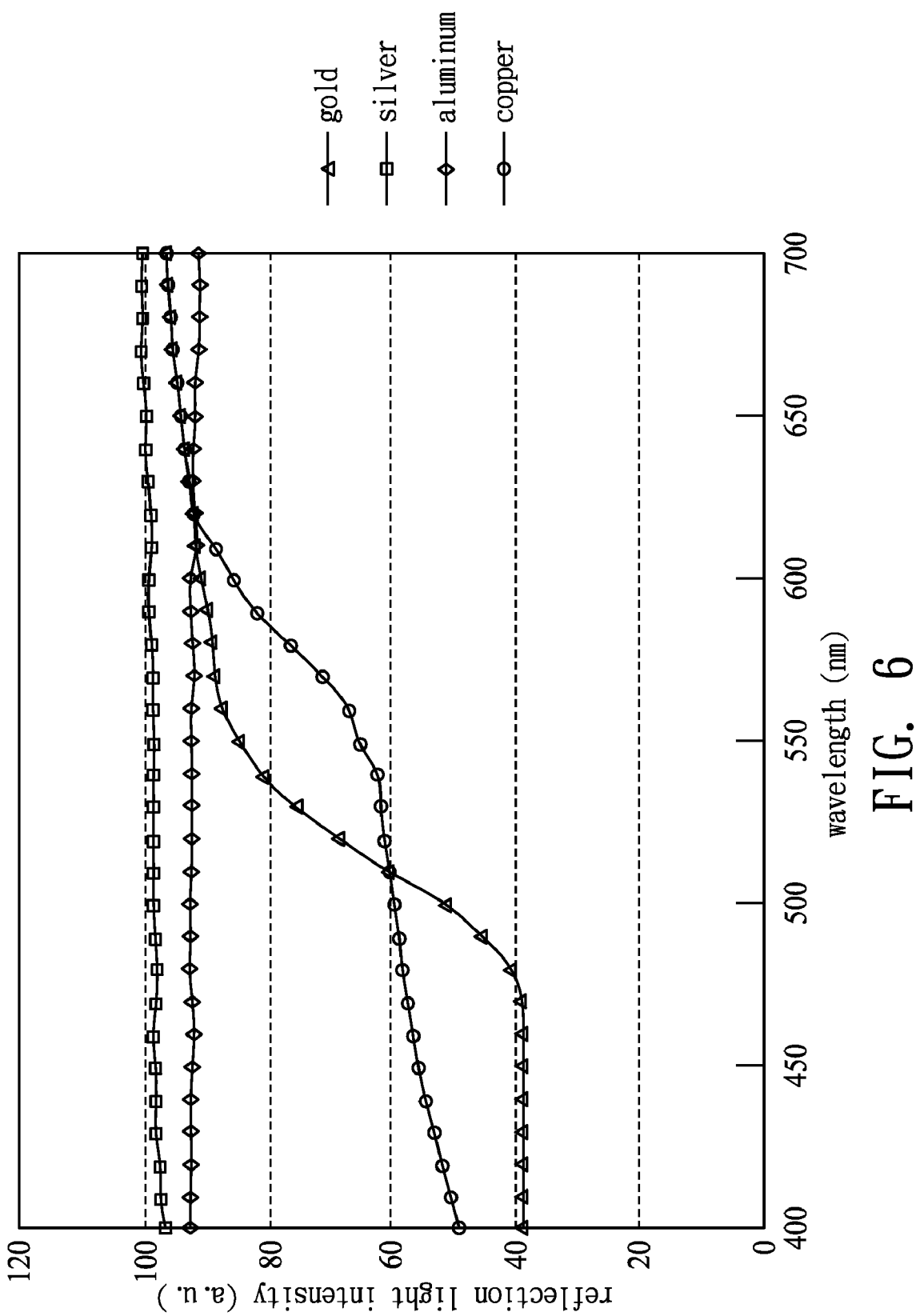
FIG. 6 shows reflection spectrums of several metallic materials.

FIG. 6 shows refection spectrums of several metallic materials. Silver and aluminum are difficult to recognize from one to another since they have very similar refection spectrums while the wavelength is between 400 and 700 nanometers. Gold and copper are easily distinguished from silver and aluminum since their refection spectrums are obviously different from those of silver and aluminum while the wavelength is between 400 and 600 nanometers. Besides, gold and copper are not difficult to recognize since they have obviously different form one to another while the wavelength is between 400 and 600 nanometers. The image sensor 42 uses the red-light charge coupled device 42A, the green-light charge coupled device 42B and the blue-light charge coupled device 42C to convert the first image and the second image (the first reflection spectrum and the second reflection spectrum) into electronic signals, and a processor can recognize the distribution of metallic materials on the sample 34 based on the different reflection intensity of the first reflection spectrum and the second reflection spectrum at different wavelengths, which can be further compared with a design diagram to inspect the defective site.

Figure 7:
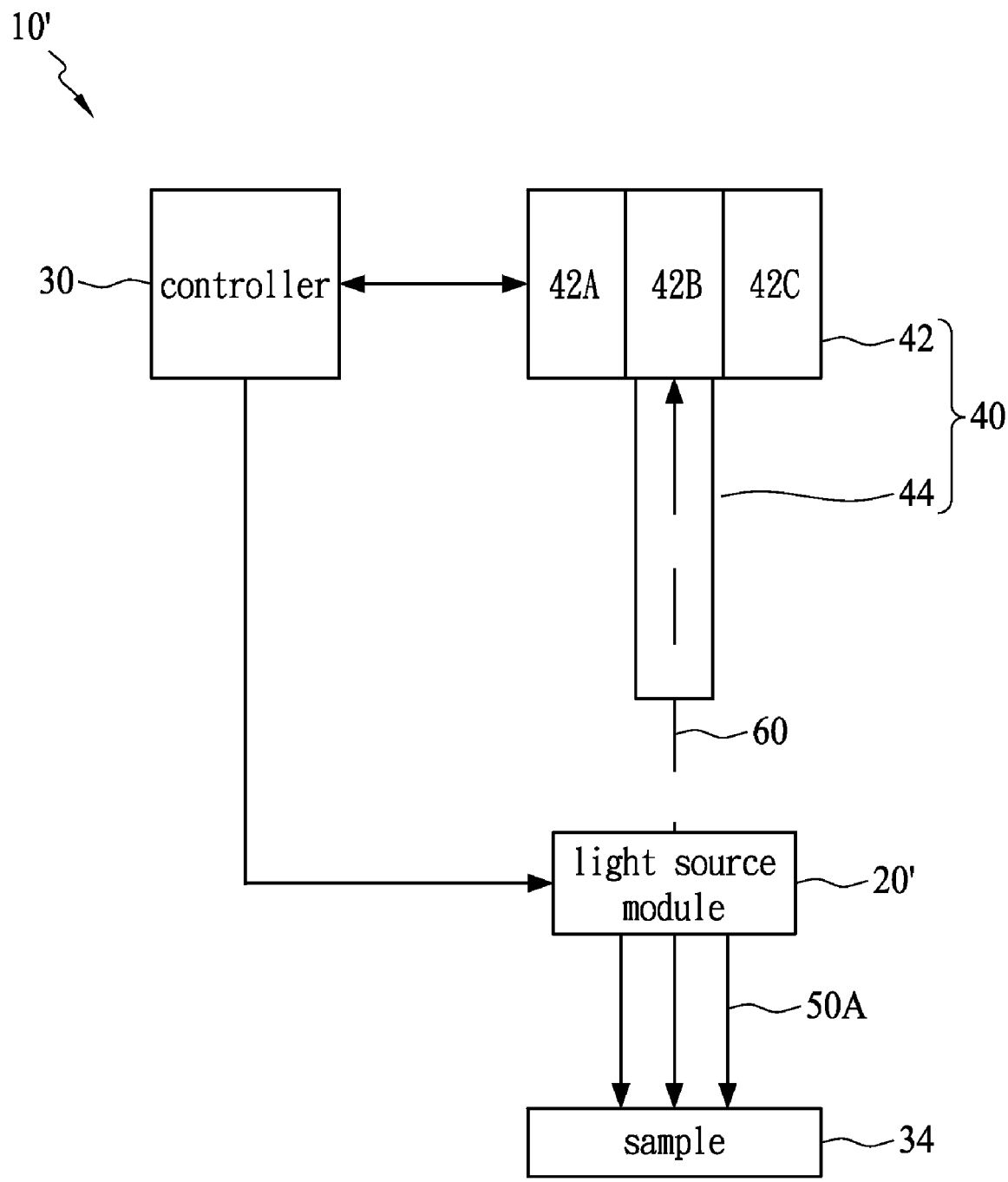
FIG. 7 and FIG. 8 illustrate an imaging system with high-spectrum resolution according to another embodiment of the present invention.
Figure 8:
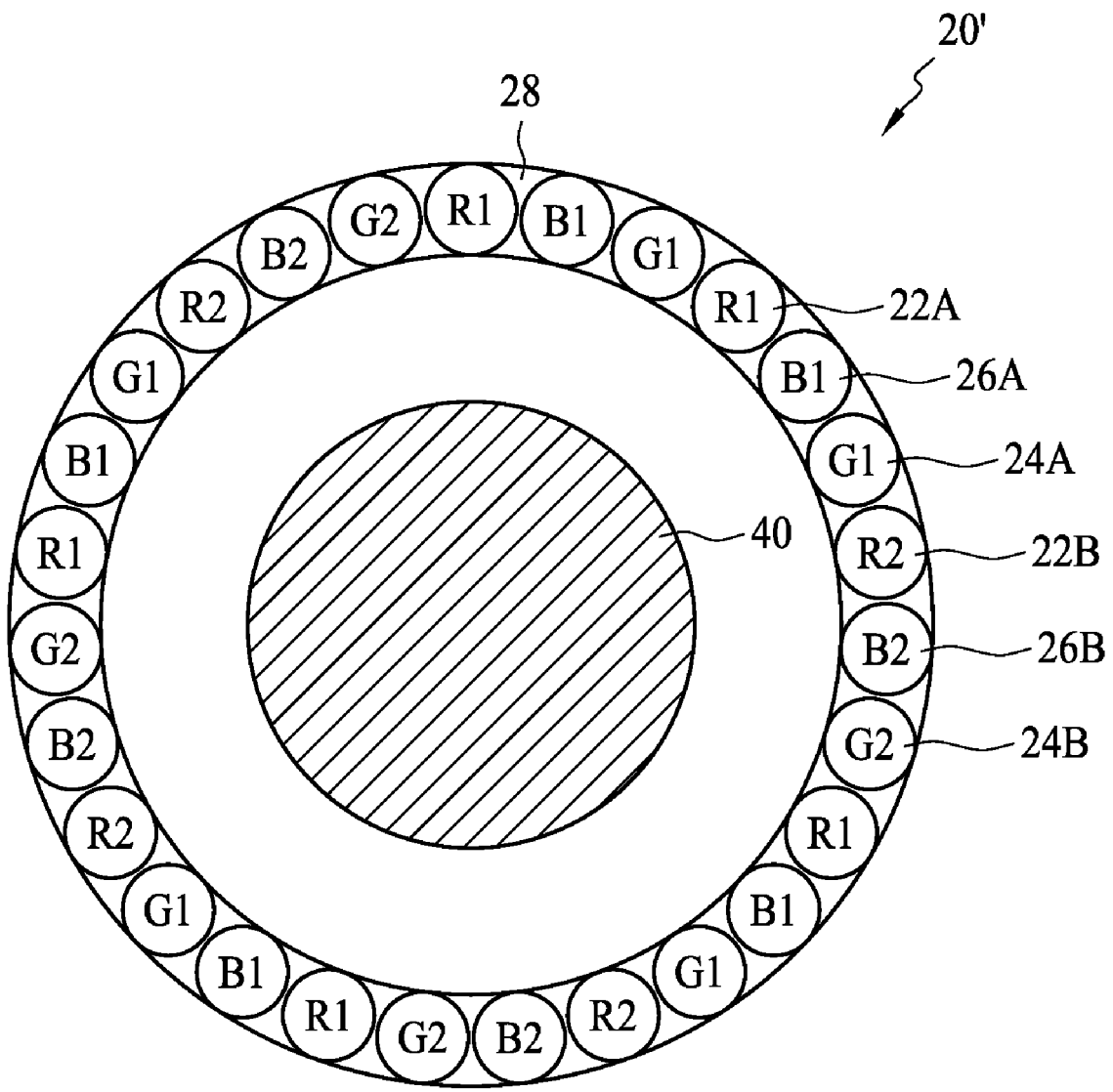

FIG. 7 and FIG. 8 illustrate an imaging system 10' with high-spectrum resolution according to another embodiment of the present invention. Compared with the imaging system 10 in FIG. 1, the imaging system 10' uses a light source module 20' having the light-emitting devices positioned in a ring-shaped region 28 and the image-capturing module positioned inside is the ring-shaped region 28. Consequently, the combination beam 50A generated by the light source module 20' can irradiate on the sample 34 without the direction of the beam-splitting device 32, and the image-capturing device 40 inside the ring-shaped region 28 can capture the reflected beam 60 from the sample 34 directly.

The present invention uses the controller 30 to drive the plurality of light-emitting diodes 22A, 22B, 24A, 24B, 26A, 26B to generate the combination beams 50A, 50B that alternately irradiate on the sample 34, and uses the charge coupled device 42A, 42B, 42C of the image-capturing module 40 to capture the reflected spectrums from the sample 34 under the irradiation of the combination beams 50A, 50B. Consequently, the present invention can capture colorful images at high speed, and the colorful images can be applied to the automatic recognition system such as the inspection of the printed circuit board, flat display and the integrated circuit package.

The above-described embodiments of the present invention are intended to be illustrative only. Numerous alternative embodiments may be devised by those skilled in the art without departing from the scope of the following claims.

What is claimed is:

1. An imaging system with high-spectrum resolution, comprising:
   a light source module including a first red light-emitting device, a second red light-emitting device, a first green light-emitting device, a second green light-emitting device, a first blue light-emitting device, and a second blue light-emitting device;
   a controller configured to control the light source module to generate a first combination beam and a second combination beam;
   an image-capturing module configured to capture a reflected beam by a sample;
   wherein the image-capturing module includes an image sensor and a lens;
   wherein the image sensor includes a red-light charge coupled device, a green-light charge coupled device and a blue-light charge coupled device;
   wherein the light-emitting devices of the light source module are positioned in a ring-shaped region;
   wherein the image-capturing module is positioned inside the ring-shaped region;
   wherein the first combination beam includes a first red light from the first red light-emitting device, the second combination beam includes a second red light from the second red light-emitting device, and the first red light and the second red light have different wavelengths;
   wherein the first combination beam includes a first green light from the first green light-emitting device, the second combination beam includes a second green light from the second green light-emitting device, and the first green light and the second green light have different wavelengths; and
   wherein the first combination beam includes a first blue light from the first blue light-emitting device, the second combination beam includes a second blue light from the second blue light-emitting device, and the first blue light and the second blue light have different wavelengths.

2. The imaging system with high-spectrum resolution of claim 1, further comprising a beam-splitting device configured to direct the combination beam to the sample and allow the reflected beam to penetrate through.

3. The imaging system with high-spectrum resolution of claim 1, wherein the light source module includes a plurality of red light-emitting devices, green light-emitting devices and blue light-emitting devices.

4. The imaging system with high-spectrum resolution of claim 1, wherein the combination beam includes a red light, a green light and a blue light.

5. The imaging system with high-spectrum resolution of claim 1, wherein the controller drives a red light-emitting device, a green light-emitting device and a blue light-emitting device of the light source module to generate the combination beam.

6. The imaging system with high-spectrum resolution of claim 1, wherein the light-emitting devices are narrowband light-emitting devices.

7. The imaging system with high-spectrum resolution of claim 6, wherein the narrowband light-emitting devices are light-emitting diodes, lasers or metal lamps.

8. An imaging method with high-spectrum resolution, comprising the steps of:
   forming a first combination beam including at least two lights of different wavelengths;
   capturing a first reflected beam of the first combination beam by a sample to have a first image;
   forming a second combination beam including at least two lights of different wavelengths;
   capturing a second reflected beam of the second combination beam by the sample to have a second image;
   determining an object according to a plurality of intensities of the first and the second reflected beams;
   wherein the first combination beam includes a first red light, the second combination beam includes a second red light, and the first red light and the second red light have different wavelengths;

wherein the first combination beam includes a first green light, the second combination beam includes a second green light, and the first green light and the second green light have different wavelengths; and wherein the first combination beam includes a first blue light, the second combination beam includes a second blue light, and the first blue light and the second blue light have different wavelengths.

9. The imaging method with high-spectrum resolution of claim 8, wherein the first combination beam and the second combination beam have different spectrums.

10. The imaging method with high-spectrum resolution of claim 8, wherein the first combination beam includes a red light, a green light and a blue light.

11. The imaging method with high-spectrum resolution of claim 8, wherein the first combination beam consists essentially of two lights of different wavelengths.

12. The imaging method with high-spectrum resolution of claim 8, wherein the first image is captured by using a charge coupled device.

13. The imaging method with high-spectrum resolution of claim 8, wherein the first combination beam is generated by using a plurality of narrowband light-emitting devices.

14. The imaging method with high-spectrum resolution of claim 13, wherein the narrowband light-emitting devices are light-emitting diodes, lasers or metal lamps.

\* \* \* \* \*